US007648957B2

(12) United States Patent
Heyden et al.

(10) Patent No.: US 7,648,957 B2
(45) Date of Patent: Jan. 19, 2010

(54) NUTRITIONAL AND THERAPEUTIC COMPOSITION OF AN INSULIN SENSITIZER AND A PEPTIDE FRACTION

(75) Inventors: Lucas Cyril Gerard van der Heyden, Leiden (NL); Lucas Johannes Cornelis van Loon, Maastricht (NL); Luppo Edens, Rotterdam (NL); Antonius Johannes Maria Wagenmakers, Birmingham (GB)

(73) Assignee: DSM IP Assets B.V., Heerlen (NL)

( * ) Notice: Subject to any disclaimer, the term of this patent is extended or adjusted under 35 U.S.C. 154(b) by 504 days.

(21) Appl. No.: 10/525,959

(22) PCT Filed: Sep. 2, 2003

(86) PCT No.: PCT/EP03/09790

§ 371 (c)(1),
(2), (4) Date: Feb. 28, 2005

(87) PCT Pub. No.: WO2004/022083

PCT Pub. Date: Mar. 18, 2004

(65) Prior Publication Data

US 2005/0271744 A1 Dec. 8, 2005

(30) Foreign Application Priority Data

Sep. 4, 2002 (EP) .................................. 02078624

(51) Int. Cl.
*A61K 38/00* (2006.01)
*A61K 51/00* (2006.01)
*A61K 38/06* (2006.01)

(52) U.S. Cl. ........................... 514/2; 424/1.69; 530/331
(58) Field of Classification Search .................... 514/2
See application file for complete search history.

(56) References Cited

U.S. PATENT DOCUMENTS

| 4,584,197 | A | 4/1986 | Takasaki et al. |
| 6,251,865 | B1 | 6/2001 | Clark et al. |
| 6,713,082 | B2 * | 3/2004 | Van Loon et al. ............ 424/439 |
| 2004/0241664 | A1 * | 12/2004 | Dekker et al. .................. 435/6 |

FOREIGN PATENT DOCUMENTS

| EP | 1172373 | * | 1/2002 |
| WO | WO 01/00223 A2 | * | 1/2001 |

OTHER PUBLICATIONS

International Search Report.

\* cited by examiner

*Primary Examiner*—Maury Audet
(74) *Attorney, Agent, or Firm*—Nixon & Vanderhye P.C.

(57) ABSTRACT

The present invention discloses a composition comprising an insulin sensitizer and a peptide fraction, which promotes significant reduction in blood glucose levels and stabilizes blood glucose levels in individuals with type 2 diabetes.

20 Claims, 8 Drawing Sheets

NUTRITIONAL AND THERAPEUTIC COMPOSITION OF AN INSULIN SENSITIZER AND A PEPTIDE FRACTION

This application is the US national phase of international application PCT/EP2003/009790 filed 2 Sep. 2003 which designated the U.S. and claims benefit of EP 02078624.0, dated 4 Sep. 2002, the entire content of which is hereby incorporated by reference.

FIELD OF THE INVENTION

The present invention relates to a composition comprising an insulin sensitizer.

BACKGROUND OF THE INVENTION

Type 2 diabetes mellitus is a clinically and genetically heterogeneous group of syndromes characterized by elevated blood glucose levels. It occurs because the insulin produced by the β (beta) cells of the pancreas is either insufficient or ineffectively utilized by target tissues, resulting in high levels of glucose in the blood. Post-prandial peaks (a rise of glucose in the body after a meal), which usually result from a high carbohydrate diet, contribute to the high blood glucose levels. Complications that surface from diabetes can usually be traced back to excessive sugar levels in the blood over a period of many years.

The progression of type 2 diabetes is often characterised as follows. At first a slow but progressive increase in insulin resistance develops. This implies that insulin production by the pancreas is normal during the early stages of the disease, but the ability of insulin to increase glucose uptake is reduced. The reduced insulin sensitivity in the early stages of the disease is usually compensated by an increased release of insulin by the pancreas. However, after several years the pancreas no longer responds properly to glucose ingestion and the reduced insulin sensitivity is accompanied by a sub-optimal insulin production. The resulting hyperglycaemia (high blood glucose level) leads to a rapid disabilitating progression of the disease and the necessity to start using oral medication and finally exogenous insulin therapy.

The abnormally high levels of glucose in the blood may contribute to various micro- and macrovascular complications, including cardiovascular disease, retinopathy, nephropathy and neuropathy. Serious health complications resulting from these high glucose levels include eye, heart, kidney, and nerve damage.

The key to fighting diabetes is through monitoring and controlling blood sugar levels. If patients conscientiously monitor and control their blood sugar level at an early stage, they may delay or prevent many complications associated with the disorder. A proper diet and exercise can help people with diabetes to maintain healthy blood glucose levels. However, when diet and exercise are inadequate to control diabetes, medication is required. At this stage treatment can still rely on the use of oral anti-diabetic drugs alone, i.e. exogenous insulin therapy is not yet necessary.

In principle three classes of oral anti-diabetes drugs are available, namely the "blocker" class, the "stimulator" class and the "sensitizer" class. The "blocker" class of oral anti-diabetes agents has been shown to delay or prevent further development of the disease. Examples of this class of agents are the so-called alpha-glucosidase inhibitors, which act by delaying the absorption of glucose from the ingested carbohydrates. The "stimulator" class of oral anti-diabetic agents stimulate the production of insulin by the pancreas. Examples of the "stimulator" class are sulfonylureas, which are known to be effective to stimulate secretion of insulin. The "sensitizer" class of oral anti-diabetic agents help to use glucose more efficiently or to make tissue cells more sensitive to insulin. Examples of pharmaceutical "insulin sensitizers" are biguanides (such as Metformin (e.g. Glucophage®) and thiazolidinediones (such as Pioglitazone (e.g. Actos®) and Rosiglitazone (e.g. Avandia®). Not surprisingly several of these oral anti-diabetic drugs have undesirable side effects. For example, adverse effects of sulphonylurea antidiabetic agents include hypoglycaemia, gastro-intestinal disturbances and hypersensitivity reactions. Adverse effects of the insulin sensitiser biguanide include gastrointestinal disturbances and lactic acidosis.

Milder insulin sensitizing effects can be obtained with a number of natural compounds. The obvious advantage of such natural insulin sensitizers is that they are convenient and safe to use. These natural insulin sensitizers can, for example, be added to our regular diet, or be added to dietary supplements and functional foods. One of these natural insulin sensitizers is chromium. Chromium is a trace mineral that is essential for normal insulin function. Dietary studies indicate that most people in the U.S. and other industrialized countries do not consume enough chromium, and deficiencies appear to be even more common in diabetic people. Many clinical studies support the benefits and safety of chromium supplementation in diabetic people. Supplemental chromium is known to lower blood insulin levels, improve glucose tolerance and decrease haemoglobin glycosylation in people with type 2 diabetes. Chromium also helps maintain healthy blood lipid levels, in particular triglycerides and HDL cholesterol. Experts, such as Richard Anderson, Ph.D. from the U.S. Dept. of Agriculture at the Beltsville Human Nutrition Research Center, recommend chromium supplementation in daily amounts of 200-1000 micrograms. Clinical studies show that in particular the organic or chelated forms, such as chromium polynicotinate, picolinate, glycine-niacin chelate, GTF chromium and chromium yeast are effective. Furthermore it has been shown that combinations of chromium and biotin (i.e. Vitamin B8) act synergistically.

Vanadium is another trace element involved in promoting normal insulin function. Some studies have shown that vanadium supplied as vanadyl sulfate can improve glucose tolerance in type 2 diabetics. Supplementation with up to 100 micrograms/day is safe, and will satisfy the body's nutritional vanadium needs including the requirement for insulin and glucose metabolism.

Niacin is another B-vitamin of special importance to diabetes. 100 milligrams/day of niacin has been shown to improve glucose tolerance and fasting blood glucose in diabetics when co-supplemented with chromium.

Fenugreek (Trigonella foenum-graecum) is a herb that is native to South East Europe, North Africa and Western Asia. The herb has been shown to be beneficial in the treatment of both type 1 and type 2 diabetes, and is thought to help control blood sugar in addition to lowering serum cholesterol levels. A dose as small as 15 mg may help to control fasting blood sugar levels as well as control sudden peaks in blood sugar following meals ['Gales Encyclopedia of Alternative Medicine', Turner J.].

Banaba Leaf Extract is a newcomer among standardized diabetes herbs and is currently sold under the trade name "Glucosol." The active compound in Glucosol, corosolic acid, has been shown to promote the transport of blood glucose into cells. Glucosol is standardized to provide a minimum of 1% corosolic acid. The extract was found to be well-tolerated and safe in human and animal studies. Compared to other herbal extracts used be people with diabetes, Glucosol offers the advantage that it can lower blood glucose in diabetic people without causing hypoglycaemia. Also, the clinically effective dose is only 32-48 milligrams daily. A series of recent and still unpublished clinical studies conducted in 1999 by Dr. W. Judy at the Southeastern Institute of Biomedical Research (Bradenton, Fla.), showed significant benefits of Glucosol when taken daily for 30 days at 32 and 48 milligrams per day. One of these studies was a randomized, double-blind crossover study with 12 diabetic subjects taking 48 milligrams of the extract. Glucosol lowered fasting blood glucose in people with type 2 diabetes, and the effect was sustained for several weeks even after discontinuation of the supplement. Study reports are available from the manufacturer (Soft Gel Technologies, Inc.) at their website (www.glucosol.com/glucosol/default.htm).

Pterostilbene, a compound found in grapes, has been identified by the USDA, and is a phytoalexin that is produced by the vines in response to stressful conditions. Studies from the Department suggest that the compound is capable of reducing blood sugar levels by up to 42%, an effect comparable to that of the antidiabetic drug metformin. Unfortunately for wine drinkers, however, it is unlikely that the compound is present in wines, due to its instability to light and air.

The potential for cinnamon in treating type 2 diabetes was first noted in August 2000. The news came from an unpublished study demonstrating that the active compound present in cinnamon, methylhydroxy chalcone polymer (MHCP), could normalise very high glucose levels in diabetic mice. Other experiments suggested this antidiabetic effect of MHCP is due to its ability to increase the cell's response to insulin, and it has been estimated that sensitivity to insulin raises by around 20 fold on administration of the chemical. Following the release of the information, researchers at the US Agricultural Research Service recommended that diabetics consume between one-quarter and one teaspoon of cinnamon per day, either alone or in foods.

Ginsenoside Re, a compound found in the ginseng berry, has been shown to be beneficial in the treatment of diabetes and obesity, helping to normalise blood sugar levels, improve insulin sensitivity and aid weight loss. Researchers, from the University of California, tested the effects of the berry on 2 groups of mice (one nondiabetic set, and a second bred to be diabetic). The berries can help to normalize blood sugar levels, improve insulin sensitivity, lower cholesterol and aid weight loss. Ginsenoside Re has been found to be one of the compounds in the berries responsible for the improved insulin sensitivity [BBC News, Monday, 10 Apr., 2000; http://news.bbc.co.uk/hi/english/health/newsid_2004000/2004255.stm].

Within the scope of the present application the term "insulin sensitizer" or "insulin sensitizing agent" refers to a compound, preferably a pharmaceutical compound or preferably a natural compound, that will lower blood glucose levels by increasing the responsiveness of the tissues to preferably insulin.

Insulin sensitizers have been shown to be effective in lowering blood glucose levels by increasing the responsiveness of target tissues to insulin. However, as the disease progresses, type 2 diabetic patients gradually loose their ability to produce sufficient insulin. This decrease in insulin production slowly diminishes the effectiveness of the insulin sensitizers, so at a certain point these patients are forced to change from natural and relatively harmless insulin sensitizers to pharmaceutical insulin sensitizers such as biguanides or thiazolidinediones and eventually drastic measures like insulin injections are required to lower blood glucose levels.

To prevent or postpone this need for pharmaceutical insulin sensitizers and finally insulin injections of diabetes type 2, there is a need for a composition that results in an effective lowering of blood glucose.

SUMMARY OF THE INVENTION

The present invention provides a composition comprising a peptide fraction which is preferably rich in di- and tripeptides in combination with an insulin sensitizer preferably a natural or pharmaceutical insulin sensitizer. This composition is very suitable as pharmaceutical or food or a food supplement. Especially this composition is useful for Type 2 diabetes. A composition comprising small peptides preferably di- and tripeptides is found to be useful to treat Type 2 diabetes.

DETAILED DESCRIPTION OF THE INVENTION

This invention pertains to compositions for the oral treatment of diabetes mellitus by lowering the levels of glucose in the blood comprising a peptide fraction along with preferably one or more insulin sensitizing agents and to methods for preparing the same. The beneficial effect of the composition according to the invention is not limited to individuals suffering from type 2 diabetes but is also recorded for healthy persons so that it can be applied in the prevention of diabetes. Moreover the composition according to the invention is useful to enhance the recovery of healthy people after physical exercise. The composition can form part of a food, a beverage or a supplement so that it can be used in the manufacture of a large variety of products including dietetic products, shakes, dietary supplements, infant nutrition, clinical nutrition, beverages such as sports drinks and soft drinks, or other foods, foodstuffs or fermented products.

The fact that the intake of intact protein has a stimulatory role on plasma insulin levels is not new but was already reported in the 1960's. Later work has identified that protein hydrolysates as well as free amino acids and especially free arginine, leucine, tyrosine and phenylalanine can have strong insulinotropic effects upon their intravenous injection. Very recently experiments have demonstrated the in-vivo insulinotropic potential of protein hydrolysates in combination with free amino acids and carbohydrate upon oral uptake (Van Loon et al, American Journal of Clinical Nutrition, 72:96-105, 2000).

We have observed that the oral intake of intact protein, or protein hydrolysates, or protein hydrolysates enriched in peptides with a molecular weight below 500 Da, or protein hydrolystes enriched in peptides with a molecular weight below 500 Da and additionally suppleted with free amino acids, leads to an increasing insulin response. Of the above-mentioned options, intake of carbohydrates in combination with intact protein leads to the lowest insulin response, intake of carbohydrates with a protein hydrolysate enriched in peptides below a molecular weight of 500 Da and additionally suppleted with free amino acids leads to the highest insulin response.

In line with this observation we have used in our Examples 1 and 4 a protein source leading to the highest insulin response i.e. a protein hydrolysate enriched in peptides below a molecular weight of 500 Da and additionally suppleted with free amino acids to demonstrate the beneficial effect of a combination with an insulin sensitiser.

At first sight type 2 diabetic patients are expected to benefit from the vigorously stimulated insulin secretion as brought about by the combined intake of protein hydrolysates, free amino acids, and carbohydrates. Although our own experiments have confirmed this stimulated insulin secretion, very much to our surprise this enhanced insulin production did not result in significant lower blood glucose levels in late stage type 2 diabetic patients. So the enhanced insulin production alone did not result in lower glucose levels. Surprisingly our experiments show that this enhanced insulin production in combination with a suitable insulin sensitizer does yield the desired lowering of blood glucose levels. Moreover, the reduction in blood glucose levels as observed with the composition according to the invention is markedly greater than the lowering effect of the sensitizer alone.

The composition according to the invention with the most potent glucose levelling effect requires that the insulin sensitizer is suitably combined with an effective amount of a specific peptide fraction. To encourage the use of the composition according to the invention in a preventive way, it is highly important that the composition combines a high palatability with low costs, i.e. the composition should be relatively cheap and have an acceptable taste.

Optimally suitable peptide fractions are obtained from protein sources having a high content of hydrophobic amino acid residues. Examples of proteins rich in hydrophobic amino acid residues are milk proteins like whey or casein, meat proteins, egg proteins, soy proteins, wheat proteins, pea proteins, potato protein, lupine protein, rice proteins and maize proteins. Preferably the protein raw material is milk protein, soy protein, or maize protein or purified fractions thereof.

In the present context, the term "peptide fraction" is understood to indicate that it may contain all types of peptides that may vary in length and optionally free amino acids. By "peptides" is meant protein molecules having a molecular weight of less than 2000 Da. Thus although the "peptide fraction" may include free amino acids, free amino acids are not included in the term "peptides". The preferred peptide fraction is characterized by a peptide size distribution in which the class of small peptides i.e. peptides with a molecular weight below 500 Da, is over-represented. In the peptide fraction according to the invention these small peptides are present for at least 30 molar %, preferably for at least 50 molar % and more preferably for at least 70 molar % of all peptides present with a molecular weight below 2000 Da. Moreover, the peptide fraction incorporated in the composition according to the invention is rich in di- and/or tripeptides. Rich in di and/or tripeptides means that at least 20 molar %, preferably at least 30 molar %, more preferably at least 35 molar % of all peptides with a molecular weight below 2000 Da is present as di- and/or tripeptides. The size distribution of the peptides composing the peptide fraction can be determined using methods as specified in the Materials & Methods section.

The peptide fraction is preferably obtained by hydrolysing a suitable protein substrate. The peptide fraction is preferably a protein hydrolysate containing a high proportion of small peptides, i.e. peptides with a molecular weight below 500 Da. Preferably these peptide fractions are obtained by enzymatic hydrolysis of a plant or animal derived protein or protein fraction.

The protein raw material may be hydrolysed by one or more hydrolytic enzymes. The hydrolytic enzyme can be of animal, plant, yeast, bacterial or fungal origin. Preferably enzyme preparations are used that have a broad cleavage specificity and a low exo-peptidase activity to minimise the liberation of free amino acids. Preferred enzymes are endoproteases, with such as subtilisin (EC3.4.24.4 or Pescalase as supplied by DSM Food Specialities, Seclin, France or Alcalase as supplied by NOVO, Bagsvaerd, Denmark), thermolysin (EC3.4.24.4 or Thermoase as supplied by Daiwa Kasei, Osaka, Japan), neutral metallo protease (EC3.4.24.28 or Brewers Protease 2000 as supplied by DSM Food Specialities, Seclin, France or Neutrase as supplied by NOVO) or trypsin (EC 3.4.21.4) or chymotrypsin (EC3.4.21.1). or papain (EC3.4.22.2) or pepsin (EC3.4.23.1). The peptide fraction that can be used to prepare a composition as disclosed in the present invention include all protein hydrolysates that can be obtained by enzymatic hydrolysis or chemical hydrolysis using common techniques as described in the literature and known to those skilled in the art.

To limit the level of bitter off-tastes that are usually generated upon the extensive hydrolysis of proteins, the peptide fraction is preferably obtained by using an amino acid, e.g. a proline-specific, protease. A proline specific protease implies preferential cleavage at either the aminoterminal or the carboxyterminal side of proline. Endoproteases capable of cleaving at the aminoterminal side of proline are known (Nature, Vol 391, 15 January 15, pp 301-304, 1998). Endoproteases with a preference for cleaving at the carboxyterminal side of proline are also known (EC3.4.21.26). The latter type of proline-specific endoprotease is preferably obtained from food-grade overproducing recombinant strains such as *Aspergillus*. An example of a suitable producer of this enzyme has been described in WO 02/45523. Furthermore proline-specific dipeptidyl-peptidases (EC 3.4.14.2) are known. The use of these proline-specific proteases in the production of the peptide fraction according to the invention has many advantages. Apart from the fact that off tastes such as bitterness are prevented, the water solubility of the peptide fraction is improved and, most importantly, the final peptide size that can be obtained is considerably reduced. Especially on protein substrates with a relatively high proline content such as wheat gluten (see Example 1) and casein (see Example 4) the incorporation of a proline-specific protease in the hydrolysis process leads to peptide fractions with relatively high proportions of peptides with a molecular weight below 500 Da.

As described in our copending patent application PCT/EP 03/05876 herein included by reference, the use of dipeptidyl- and/or tripeptidyl-peptidases (EC 3.4.14) in the production of hydrolysates is of special importance as these offer an efficient way for producing the peptide fraction according to the invention. Therefore preferably the peptide fraction is a hydrolysate preferably comprising a significant amount of di- and/or tripeptides.

As the result of the action of the various proteases used, the peptide fraction is likely to contain free amino acids as well. The amount of free amino acids resulting from the enzymatic hydrolysis reaction may range from 1 to 10 wt % of the peptides having a MW of below 2000 Da present calculated on dry weight.

Apart from obtaining the peptide fraction by protein hydrolysis, the peptide fraction can be obtained via chemical or enzymatic synthesis. Moreover a hydrolysate spiked with such synthesised peptides can form the peptide fraction as present in the composition according to the invention.

Preferably the peptide fraction is present in the composition according to the invention in an amount of 0.5-99 wt %, preferably 1.0-90 wt %, more preferably 1.5-50 wt. %, calculated on the basis of the dry weight of the composition.

By 'insulin sensitizing agent' or 'insulin sensitizer' is meant a compound that will lower blood glucose levels by increasing the responsiveness of the tissues to insulin. Examples of "natural" insulin sensitizing agents are minerals preferably chromium, vanadium or a B-vitamins like niacin. Furthermore herbs or plant extracts preferably from Banaba leaf, ginseng berry, cinnamon and certain compounds in grapes have been shown to be effective insulin sensitizers.

Also the active compounds identified in these herbs and plant extracts and thought to be responsible for these insulin sensitising effects are preferably applied as natural sensitizers: corosolic acid, pterostilbene, methylhydroxy chalcone polymer (MHCP) and Ginsensoside Re. Preferred examples of pharmaceutical "insulin sensitizers" are biguanides (such as Metformin (e.g. Glucophage®) and thiazolidinediones (such as Pioglitazone (e.g. Actos®) and Rosiglitazone (e.g. Avandia®)). These natural insulin sensitizers be preferably added to products in quantities according to their "Reference Daily Intake" or even higher, depending on the person's nutritional need. A list for Reference Daily Intake values is included in the FDA's Code of Federal Regulations 21 CF 101.9, Apr. 1, 2001 which includes those nutrients for which a RDI has been established [http://vm.cfsan.fda.gov/~lrd/CFR101-9.HTML].

The composition according the invention may contain a single insulin sensitizing agent or combinations of such agents. Preferably the composition according to the invention contains these agents in their recommended daily dosages or higher. The composition according to the invention may contain the peptide fraction and the insulin sensitizer in a mixed form or the peptide fraction and insulin sensitizer may be a separately packed and sold as a one package. Also the use of the composition according to the invention in combination with a pharmaceutical insulin sensitiser may be recommended.

Apart from peptides and the insulin sensitizing agent, the composition may optionally contain free amino acids.

Free amino acids belonging to the group of leucine and/or arginine and/or phenylalanine and/or tyrosine are of particular importance. These free amino acids may be added to the peptide fraction to obtain the composition according to the invention. Because in some countries the addition of extra free amino acids is not allowed, the desired balance between the bound and free amino acids can also be obtained using selective combinations of an endoprotease plus an exoprotease as outlined in WO02/32232. In this case the free amino acids present have been obtained by a further proteolytic breakdown of the peptide fraction and form an integral part of the peptide fraction. Preferred compositions are rich in amino acids from the group of leucine and/or arginine and/or phenylalanine and/or tyrosine. Preferably the total of the free and peptide bound amino acids belonging to the group of leucine, arginine, phenylalanine and tyrosine are present in the composition of the invention in at least 10% wt, preferably at least 20% wt, more preferably at least 30% wt, still more preferably at least 50 wt % and most preferably at least 60 wt %, calculated on the basis of the dry weight of the total of free and peptide bound amino acids. Preferably the amino acids from this group are present in the composition in an amount of 0.5-99 wt %, preferably 1.0-90 wt %, more preferably 1.5-50 wt %, calculated on the basis of the dry weight basis of the composition.

The level of free amino acids as well as the total content of amino acids present in the final composition can be established using methods specified in the Materials & Methods section.

Apart from amino acids, carbohydrates are optionally present in the composition according to the invention. Depending upon the anticipated use, i.e. as such or in combination with other food, the composition may contain a separate source of carbohydrates. These carbohydrates can be glucose or more slowly absorbed carbohydrates like maltodextrins or starch depending upon the desired glycaemic-index for the particular application. In the composition of the invention, carbohydrates can be present in an amount of 1.0- 90% wt, preferably 2-50% wt, more preferably 6-35% wt calculated on the basis of dry weight of the composition.

The wide range of carbohydrate content of the composition according to the invention can be explained by different anticipated uses of the composition.

On the one hand, an optimized formulation for consumers that prefer to take the composition alongside their carbohydrate containing meal or even prefer to take the composition in between meals is an almost pure peptide and insulin sensitizer supplement, e.g. in the form of a tablet, a syrup or a sachet.

On the other hand, the composition may be formulated so that it can be integrated in a carbohydrate containing regular meal or "approved meal".

Other optional components of the composition according to the invention are vitamins, minerals, flavours, antioxidants, components having co-enzyme and antioxidant properties, lipids including emulsifiers, colorants, and proteins for meeting specific nutritional and/or physiological needs.

The composition of the present invention can be either a pharmaceutical composition or a food composition.

The composition according to the invention may be a solid of liquid. The composition may have the form of a powder, a tablet, a capsule, other galenic forms, a beverage or any other food product.

The composition of the present invention may be part of a normal meal or part of an approved meal.

By "approved meal" or "approved diabetic diet" is meant a meal recommended or approved by a national nutritional organization for the health of a diabetic, for example, the American Diabetes Association Inc. ("ADA"). For example the meals recommended in "Maximizing the Role of Nutrition in Diabetes Management" published 1994 by the American Diabetes Association, Inc., are "approved meals". Other Western organizations, which recommend or approve a meal for a diabetic, are The International Diabetes Federation; the European Association For the Study of Diabetes; and the European and Canadian Dietetic Association. Other Eastern and Far Eastern organizations are the Chinese Diabetes Federation; the Japanese Diabetes Federation; and the Indian Diabetes Federation. It will be appreciated that an "approved meal" will vary depending upon the culture and geography of the diabetic. However, it is understood that, irrespective of either culture of geography, a compliant diabetic will eat a meal which makes no more than a reasonable demand upon his/her system.

LEGENDS TO THE FIGURES

EXAMPLES

Materials and Methods

Figure 1:
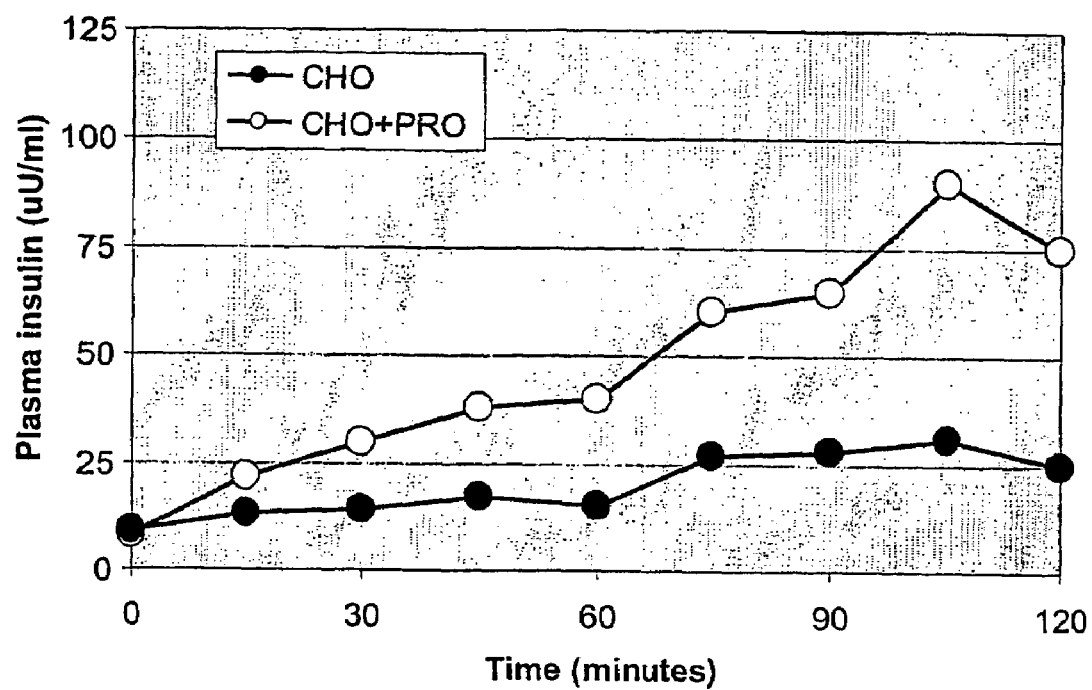
FIG. 1 shows the Plasma insulin response (microUnits/ml) for type 2 diabetic patients in minutes after drinking a beverage containing carbohydrate (CHO) or carbohydrate plus peptides and free amino acids (CHO+PRO) respectively.

Sodium caseinate containing 90% protein was obtained from DMV International (The Netherlands). Wheat gluten was obtained from Cargill. L-Leucine, L-Phenylalanine, beta-lactoglobulin and crude lactalbumin were obtained from Sigma-Aldrich.

Subtilisin from *B. licheniformis* (Delvolase®), 560 000 DU per gram) was obtained from DSM Food Specialities (Seclin, France).

Enzyme Activity

Overproduction and chromatographic purification of the proline specific endoprotease from *Aspergillus niger* was accomplished as described in WO 02/45524. The activity of the latter enzyme was measured according to the method described in Japanese patent JP5015314 with minor modifications. Briefly, the enzymatic activity was tested on Z-Gly-Pro-pNA at 37 degrees C. in a citrate/disodium phosphate buffer pH 5. pH 5.0 was chosen because the pH optimum of the enzyme is below pH 6 in this test. The reaction product was also monitored spectrophotometrically at 410 nM. Overproduction and chromatographic purification of the tripeptidylpeptidase TPAP-A encoded by gene 12 from *Aspergillus niger* was accomplished as described in EP 02100667.1. The activity of the purified tripeptidyl aminopeptidase was measured in a similar way. However, in this case the synthetic substrate Ala-Ala-Phe-pNA (Bachem, Switzerland) was used in an incubation in 0.1 mol/litre citrate buffer at pH 4.0 and 60 degrees C. The purified TPAP-A had an activity of 8 units/ml.

A unit is defined as the quantity of enzyme that provokes the release of 1 μmol of p-nitroanilide per minute under these conditions.

The Degree of Hydrolysis (DH) as obtained during incubation with the various proteolytic mixtures was monitored using a rapid OPA test (JFS, Vol 66, NO 5, 2001).

The average peptide chain length in the various peptide fractions was determined by chromatography over a Superdex Peptide HR 1030 column.

Sensoric Evaluation of Peptide Fraction "Bitterness"

Sensoric evaluation of the various peptide fractions was carried out by an independent panel trained in detecting and ranking various levels of bitterness. During the sessions, the taste trials were performed 'blind' and bitterness was scored on a scale from 0 (none)-4 (very bitter). Panel members were trained with quinine sulphate with the following solutions:

15 ppm quinine sulphate>Intensity bitter=1
20 ppm quinine sulphate>Intensity bitter=2
30 ppm quinine sulphate>Intensity bitter=3
50 ppm quinine sulphate>Intensity bitter=4

Peptide size distribution of peptide fractions

The content of peptides with a molecular weight below 500 kDa is estimated using a HPSEC method using a Superdex HR10/30 Amersham Pharmacia (range 100-7000 Da) in combination with the required reference molecules. The content of di- and tripeptides is estimated using the volatile ion-pairing reagent NFPA in combination with reversed phase liquid chromatography as described in the LC/MS analysis section.

LC/MS Analysis

HPLC using an ion trap mass spectrometer (Thermoquest®, Breda, the Netherlands) coupled to a P4000 pump (Thermoquest®, Breda, the Netherlands) was used in characterising the enzymatic protein hydrolysates produced by the inventive enzyme mixture. The peptides were separated using a PEPMAP C18 300A (MIC-15-03-C18-PM, LC Packings, Amsterdam, The Netherlands) column in combination with a gradient of 0.1% formic acid and 1 mM nonafluoropentaoic acid (NFPA) in Milli Q water (Millipore, Bedford, Mass., USA; Solution A) and 0.1% formic acid in acetonitrile (Solution B) for elution. The gradient started at 95% of Solution A and increased to 40% of solution B in 140 minutes and was kept at the latter ratio for another 5 minutes. The injection volume used was 50 microliters, the flow rate was 50 microliter per minute and the column temperature was maintained at 30° C. The protein concentration of the injected sample was approximately 50 micrograms/milliliter.

Detailed information on the individual peptides was obtained by using the "scan dependent" MS/MS algorithm, which is a characteristic algorithm for an ion trap mass spectrometer.

Full scan analysis was followed by zoom scan analysis for the determination of the charge state of the most intense ion in the full scan mass range. Subsequent MS/MS analysis of the latter ion resulted in partial peptide sequence information, which could be used for database searching using the SEQUEST application from Xcalibur Bioworks (Thermoquest®, Breda, The Netherlands). Databanks used were extracted from the OWL.fasta databank, available at the NCBI (National Centre for Biotechnology informatics), containing the proteins of interest for the application used. In those experiments in which well characterized protein substrates such as whey proteins or caseins were measured, the precision of the analysis technique was increased by omitting those MS/MS spectra with a sequence fit of less than 50%.

By using different enzyme mixtures the mass range of the peptides formed started at di- and tripeptides. By using the volatile ion-pairing reagent NFPA in combination with reversed phase liquid chromatography smaller and more hydrophilic peptides with a mass ranging from approx. 200 to 2000 Daltons can be monitored. This was considered suitable for further analysis by MS sequencing.

Angiotensin (M=1295.6) was used to tune for optimal sensitivity in MS mode and for optimal fragmentation in MS/MS mode, performing constant infusion of 60 mg/ml, resulting in mainly doubly and triply charged species in MS mode, and an optimal collision energy of about 35% in MS/MS mode.

Determination of Amino Acids

A precisely weighed sample of the proteinaceous material was dissolved in dilute acid and precipitates were removed by centrifugation in an Eppendorf centrifuge. Amino acid analysis was carried out on the clear supernatant according to the PicoTag method as specified in the operators manual of the Amino Acid Analysis System of Waters (Milford Mass., USA). To that end a suitable sample was obtained from the liquid, added to dilute acid and homogenized. From the latter solution a new sample was taken, dried and derivatised using phenylisothiocyanate. The various derivatised amino acids present were quantitated using HPLC methods and added up to calculate the total level of free amino acids in the weighed sample.

To relate this total level of free amino acids in the sample to the total level of amino acids that can be liberated from this sample, the sample is also subjected to acid hydrolysis followed by a quantification of the total free amino acids present as detailed above. Since during acid hydrolysis Trp and Cys are destroyed, these amino acids are not included in the data presented. However, Gln and Asn residues are converted into Glu and Asp during acid hydrolysis so that the values for Glu and Gln, and for Asp and Asn were usually summed together to allow comparison with the data obtained before acid hydrolysis.

Example 1

Peptides Enriched with Di- and Tripeptides and Amino Acids Enhance Plasma Insulin Levels but do not Diminish High Glucose Levels in Diabetic Patients The aim of this study was to investigate if a peptide fraction enriched with free leucine and phenylalanine could significantly lower blood glucose levels in type 2 diabetic patients.

Subjects

Ten (long-term) diagnosed male type 2 diabetic patients were selected to participate in this study. Exclusion criteria were impaired renal or liver function, obesity (BMI>30), cardiac disease, hypertension, diabetic complications and (exogenous) insulin therapy. Most subjects (n=8) were using oral antidiabetics. In the diabetic subjects, antidiabetic medication was withheld for 3 days before participation in the trials and throughout the entire experimental period. Subjects were screened for glucose intolerance/type 2 diabetes by an oral glucose tolerance test (OGTT) according to the World Health Organisation criteria of 1999.

Study Design

Each subject participated in 2 trials, separated by one week, in which the insulin response and the glucose response to the ingestion of 2 drink compositions (CHO or CHO+PRO; see below for definitions) was determined. Both trials lasted 2 hours in which subjects were seated and remained inactive. Drinks were provided in randomised order and double blind.

Protocol

Experiments were carried out at 8:30 A.M after an overnight fast. A Teflon catheter was inserted into an antecubital vein and a resting blood sample was drawn (t=0 minutes). Immediately thereafter subjects drank an initial bolus (3 ml.kg$^{-1}$) of a given test drink (CHO or CHO+PRO trial). Repeated boluses (3 ml.kg$^{-1}$) were taken every 30 minutes until t=90 minutes. Blood samples were drawn at 15 minutes intervals for measurement of plasma glucose and insulin concentrations.

Beverages

At t=0, t=30, t=60 and t=90 subjects received a beverage volume of 3 ml/kg body weight to ensure a given dose of 0.8 g/kg body weight/hour carbohydrate (50% glucose; 50% maltodextrin) without or with an additional 0.4 g/kg body weight/hour of a peptide fraction (CHO or CHO+PRO trial, respectively). This peptide fraction consisted of an extensively hydrolysed wheat protein (0.2 g/kg body weight/hour) suppleted with free leucine (0.1 g/kg body weight/hour) as well as free phenylalanine (0.1 g/kg body weight/hour). So half of the nitrogen as supplied by the beverage was supplied by wheat protein peptides, one quarter by the free leucine and another quarter by the free phenylalanine.

Analysis

Blood (10 ml) was collected in EDTA containing tubes and centrifuged at 1000 g and 4° C. for 10 minutes. Aliquots of plasma were frozen immediately in liquid nitrogen and stored at −80° C. Glucose (Unit Kit III, 07367204, Roche, Basel, Switzerland) was analysed with the COBAS FARA semi automatic analyser (Roche, Basel, Switzerland). Insulin was analysed by radio-immuno-assay (Insulin RIA 100 kit, Pharmacia, Sweden).

Figure 2:
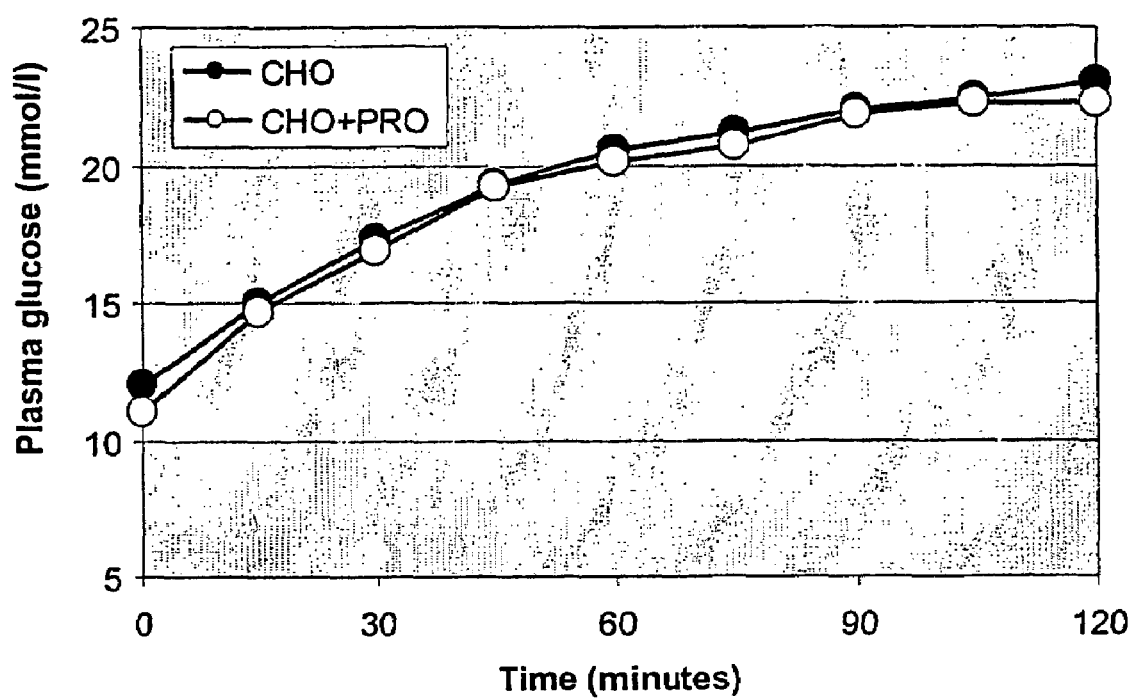
FIG. 2 shows the Plasma glucose response (mmol/l) for type 2 diabetic patients in minutes after drinking a beverage containing carbohydrate (CHO) or carbohydrate plus peptides and free amino acids (CHO+PRO) respectively.

According to the results obtained (see FIG. 1) the insulin responses of the type 2 diabetic patients were substantially increased by the inclusion of the peptide fraction (PRO) mixture in the drink. The insulin levels increased to 289% of the original 100% (P<0.01). The results showed that while keeping the glucose intake the same, addition of the peptide fraction results in a normalisation of the insulin response in type 2 diabetics (see FIG. 1). However, unlike the insulin response, plasma glucose concentrations were not differently affected between trials within this timeframe (see FIG. 2)

These observations lead to the surprising observation that although the insulin response in long-term diagnosed type 2 diabetic patients was substantially enhanced by the addition of the peptides plus free amino acids, no significant lowering effect was observed on their blood glucose concentrations.

Example 2

Beta-Casein Hydrolysates Obtained by a Proline-Specific Endoprotease in Combination with a Tripeptidyl Aminopeptidase Contain High Proportions of Tripeptides as Well as Peptides Having Carboxyterminal Proline Residues To allow a more precise LC/MS/MS analysis of the various reaction products obtained by combining a proline-specific endoprotease with a tripeptidylpeptidase on proline rich protein substrates such as wheat gluten or casein, another hydrolysis experiment was carried out in which pure bovine beta casein was used as the substrate. To that end a 0.2% (w/w on protein) solution was prepared by dissolving pure beta-casein (Sigma) in water and adjusting the pH to 8.0 by NaOH. Then the serine protease subtilisin (Delvolase) was added to a concentration of 5% (volume of the commercial enzyme product per weight of beta-casein) and the mixture was incubated for 1 hour at 60 degrees C. under non-pH-stat conditions. The reaction was stopped by lowering the pH to 5.5 using lactic acid followed by a heat treatment of 10 minutes at 90 degrees C. Then the mixture was cooled down to 50 degrees C. and a sample was taken for LC/MS/MS analysis. A subsequent incubation with the proline-specific endoprotease (EndoPro) from *A. niger* (see WO 02/45523) was carried out by adding a chromatographically purified solution of the overproduced proline specific endoprotease from *A. niger* in a concentration of 20 units/gram protein. After incubating for 2 hours at 50 degrees C. under non-pH-stat conditions the proline specific endoprotease was inactivated by another heat treatment to yield another sample for LC/MS/MS analysis. Finally chromatographically purified TPAP-A (see EP 02100667.1) was added in a concentration of 4 units per gram substrate and the incubation was continued for 2 hours at 60 degrees C. and then inactivated by heating to yield another LC/MS/MS sample. Subsequent incubations were carried out on beta-casein without Delvolase using the proline-specific endoprotease and TPAP-A, either alone or in combination, under the above described conditions. The latter samples were also subjected to LC/MS/MS analysis. The data obtained are shown in the Table underneath.

| Enzymes used to prepare beta-casein hydrolysate | Number of peptides analysed | Peptides with C-terminal -Pro (molar % of all peptides analysed) | Di + tripeptides (molar % of all peptides analysed) | Tripeptides (molar % of all peptides analysed) |
|---|---|---|---|---|
| Subtilisin | 93 | 0 | 12 | 6 |
| Subtilisin + EndoPro | 68 | 41 | 34 | 25 |
| Subtilisin + EndoPro + TPAP-A | 69 | 36 | 45 | 36 |
| EndoPro | 55 | 49 | 11 | 11 |
| TPAP-A | 1 | 0 | 100 | 100 |
| EndoPro + TPAP-A | 68 | 40 | 43 | 40 |

Despite the broad specificity of the TPAP-A enzyme used (see EP 02100667.1), incubating the pure beta-casein with just the TPAP-A enzyme results in the release of a single peptide only, i.e. the N-terminal tripeptide Arg-Glu-Leu of beta-casein. For an unknown reason the TPAP-A enzyme used cannot remove the next tripeptide from this substrate hereby clearly demonstrating the need for combining the TPAP with an endoprotease such as subtilisin or a proline specific endoprotease or a combination of the two. The results shown above clearly indicate that such combinations of a tripeptidylpeptidase with one or more endoproteases lead to a considerable increase in the number of tripeptides generated. Combinations involving proline specific endoproteases all show an impressive increase in the number of peptides having carboxyterminal proline residues from which a reduced bitterness may be inferred (see WO 02/45523).

Example 3

Benefits of Combining a Proline-Specific Endoprotease with a Tripeptidylpeptidase on Substrates Low in Proline Here we demonstrate that the enzyme combination of a proline-specific endoprotease in combination with a tripeptidyl peptidase is also beneficially used in the hydrolysis of substrates with lower proline contents.

A crude lactalbumin fraction from bovine milk (Sigma) was suspended in water in a concentration of 20 grams/liter after which the pH was adjusted to 8.0. The serine protease subtilisin (Delvolase) was added to a concentration of 4% (volume of the commercial enzyme product per weight of the substrate) and the mixture was incubated for 2 hours at 60 degrees C. under non-pH-stat conditions. Then the pH of the suspension was lowered to pH to 4.5 using citric acid and divided into 4 portions. One portion was heated to inactivate the Delvolase enzyme and then kept frozen until LC/MS/MS analysis. To the other three portions either the chromatographically purified proline specific endoprotease from *A. niger* (EndoPro) was added (1 unit/gram lactalbumin) or tripeptidylpeptidase (TPAP-A; 20 units/gram of lactalbumin) or a combination of proline specific endoprotease and TPAP-A (1 unit+20 units/gram lactalbumin; see Materials&Methods for unit definitions). The mixtures were incubated overnight at 50 degrees C., subjected to a heat treatment to inactivate the enzymes and stored at −20 degrees C. Samples were first centrifuged and the clear supernatant was used for LC/MS/MS analysis. Only those peptides fitting with the amino acid sequence of alpha-lactabumin were taken into account.

The LC/MS/MS data obtained are shown in FIGS. 5, 6, 7 and 8: peptide length in amino acid residues is depicted on the X-axis and on the Y-axis the number of peptides analysed. Even without a recalculation of peptides of a specific length into percentages of the total peptides analysed, the benefits of an incubation with either an proline-specific endopeptidase or a tripeptidyl peptidase or a combination of these two enzymes, become visible. Together with the results provided in the previous Example the data obtained clearly demonstrate that the combination of a proline-specific endoprotease with a tripeptidyl peptidase provides hydrolysates enriched in peptides with a molecular weight below 500 Da and, more specifically, enriched in di- and tripeptides, be it on proline-rich or on other proteinaceous substrates Example 4

Peptides Enriched with Di- and Tripeptides Combined with an Insulin Sensitizer Raise Plasma Insulin Levels and Diminish High Glucose Levels in Diabetic Patients The aim of this study is to investigate if a peptide fraction according to the invention in combination with an 'insulin sensitizer' can raise the insulin response in type 2 diabetic patients, thereby lowering blood glucose levels. The peptide fraction used was obtained by extensively hydrolysing sodium caseinate to obtain a peptide fraction containing more than 70 molar % of peptides with a molecular weight below 500 Da suppleted with levels of free leucine and free phenylalanine identical to the levels used in Example 1.

Subjects

Six (long-term) diagnosed male type 2 diabetic patients all using oral 'insulin sensitizer' drugs (but no exogenous insulin) are selected to participate in this study. Exclusion criteria are impaired renal or liver function, obesity (BMI>30), cardiac disease, hypertension, diabetic complications and (exogenous) insulin therapy.

Each subject participates in 2 trials, separated by one week, in which the insulin and glucose response to the ingestion of 2 beverage compositions (Carbohydrate (CHO) or Carbohydrate+Peptide fraction according to the invention (CHO+PRO)) is determined while the diabetic patients maintain their usual 'insulin sensitizer' therapy. Both trials last 3 hours in which subjects are seated and are remained inactive. Drinks are provided in randomised order and double blind.

Protocol

Experiments are carried out at 8:30 A.M. after an overnight fast. A Teflon catheter is inserted into an antecubital vein and a resting blood sample is drawn (t=0 minutes). Immediately thereafter subjects drink an initial bolus (3 ml.kg−1) of a given test drink (CHO or CHO+PRO trial). Repeated bolusses (3 ml.kg−1) are taken every 30 minutes. Blood samples are drawn at 15 minutes intervals for measurement of plasma glucose and insulin concentrations.

Beverages

Beverage volumes and dosages of carbohydrate (CHO) and carbohydrate plus peptides and free amino acids (CHO+PRO) were as described in Example 1.

Analysis

Blood samples (10 ml) are collected in EDTA containing tubes and centrifuged at 1000 g and 4 degree Celsius for 10 minutes. Aliquots of plasma are frozen immediately in liquid nitrogen and stored at −80 degree Celsius. Glucose (Unit Kit III, 07367204, Roche, Basel, Switzerland) is analysed with the COBAS FARA semi automatic analyser (Roche, Basel, Switzerland). Insulin is analysed by radio-immuno-assay (Insulin RIA 100 kit, Pharmacia, Sweden).

Figure 3:
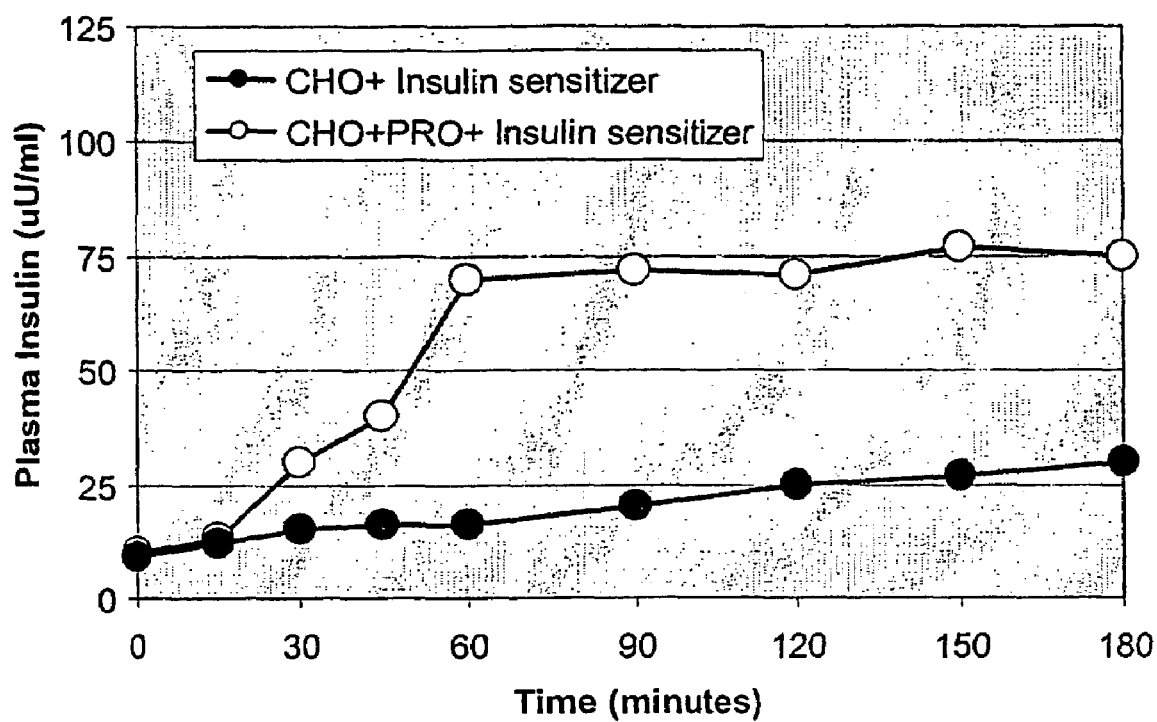
FIG. 3 shows the Plasma insulin response (microUnits/ml) for type 2 diabetic patients in minutes after drinking a beverage containing carbohydrate (CHO+insulin sensitiser) or carbohydrate plus peptides and free amino acids (CHO+PRO+insulin sensitiser) while taking an insulin sensitizer simultaneously.
Figure 4:
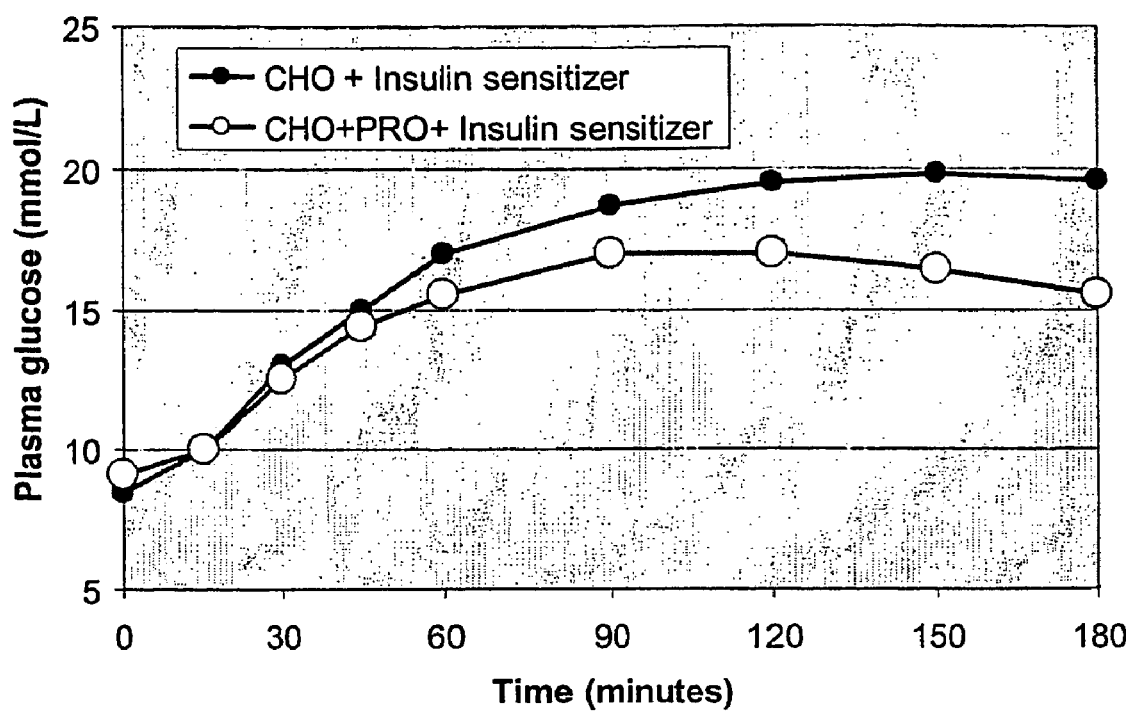
FIG. 4 shows the Plasma glucose response (mmol/l) for type 2 diabetic patients in minutes after drinking a beverage containing carbohydrate (CHO+insulin sensitiser) or carbohydrate plus peptides and free amino acids (CHO+PRO+insulin sensitiser) while taking an insulin sensitizer simultaneously.
Figure 5:
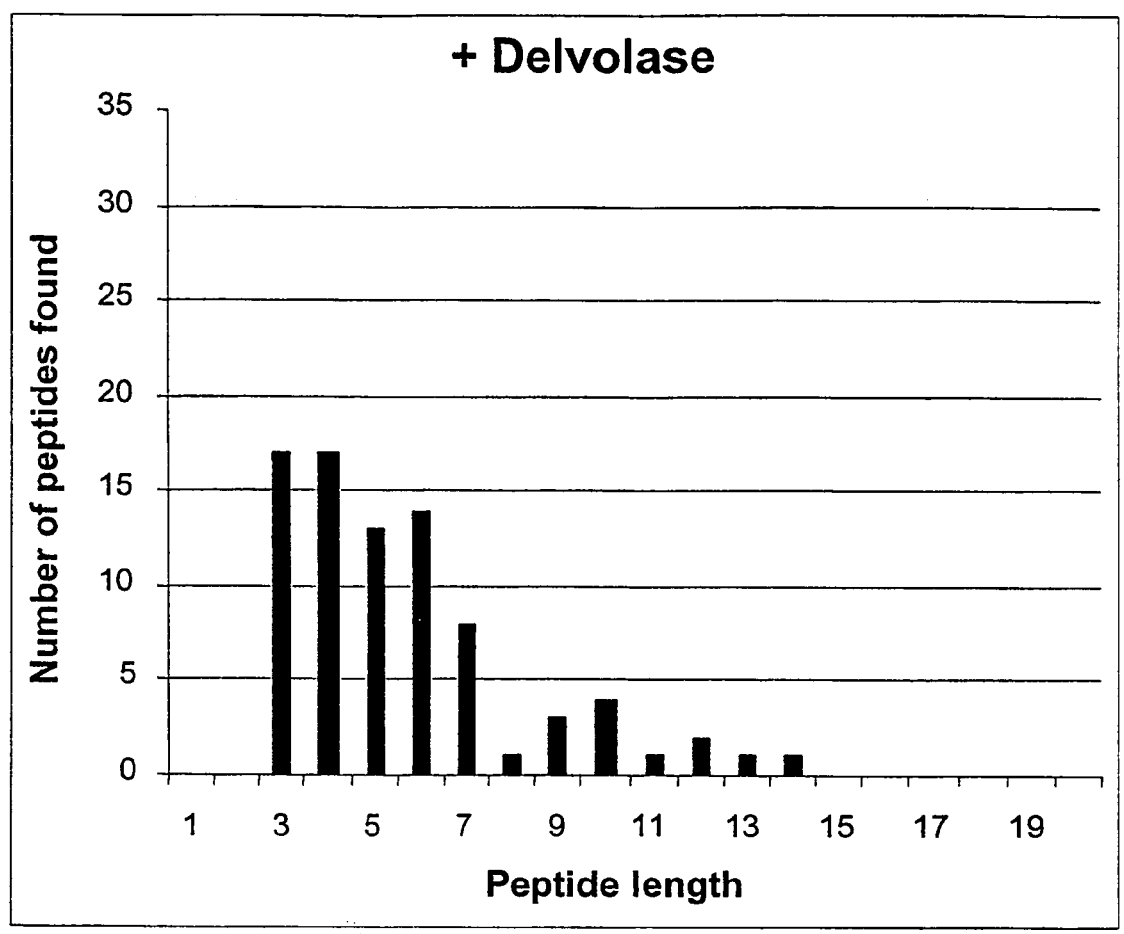
FIG. 5 shows LC/MS/MS data of a lactalbumin hydrolysate, obtained using Delvolase
Figure 6:
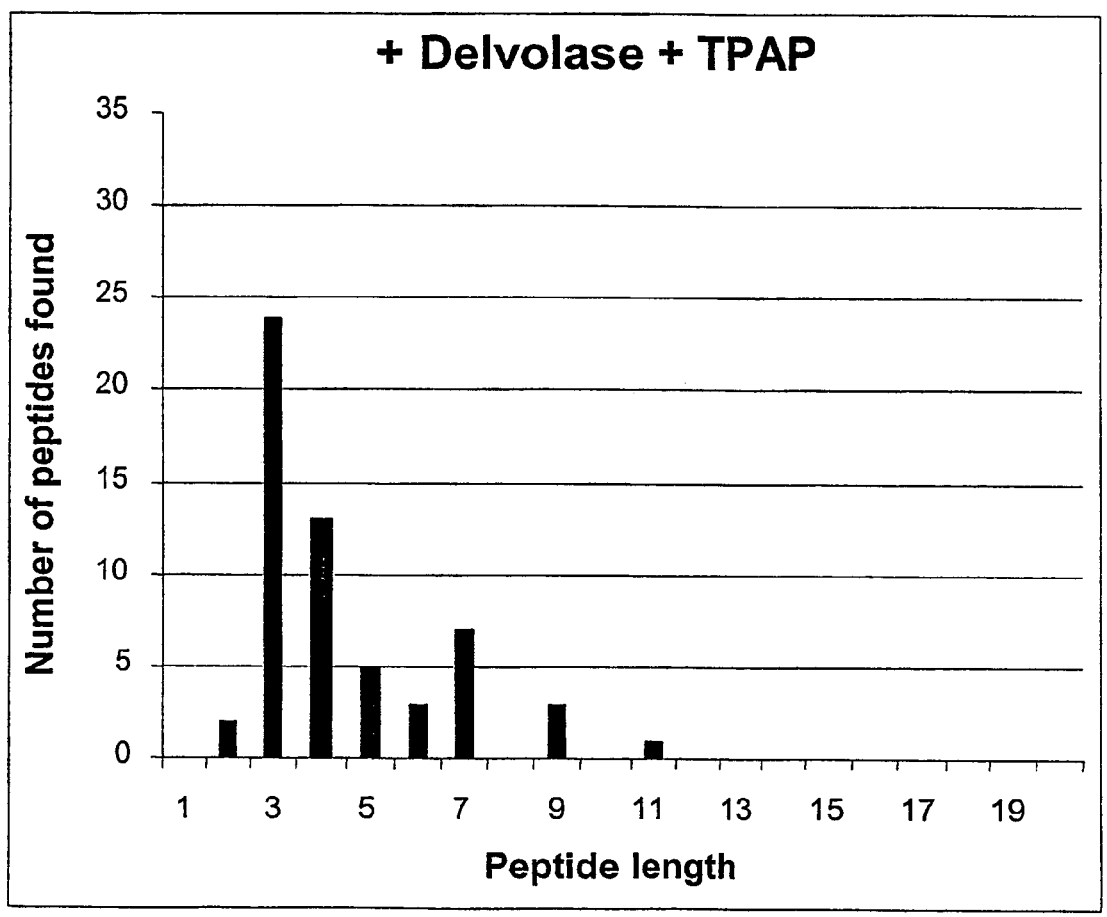
FIG. 6 shows LC/MS/MS data of a lactalbumin hydrolysate, obtained using Delvolase+TPAP-A
Figure 7:
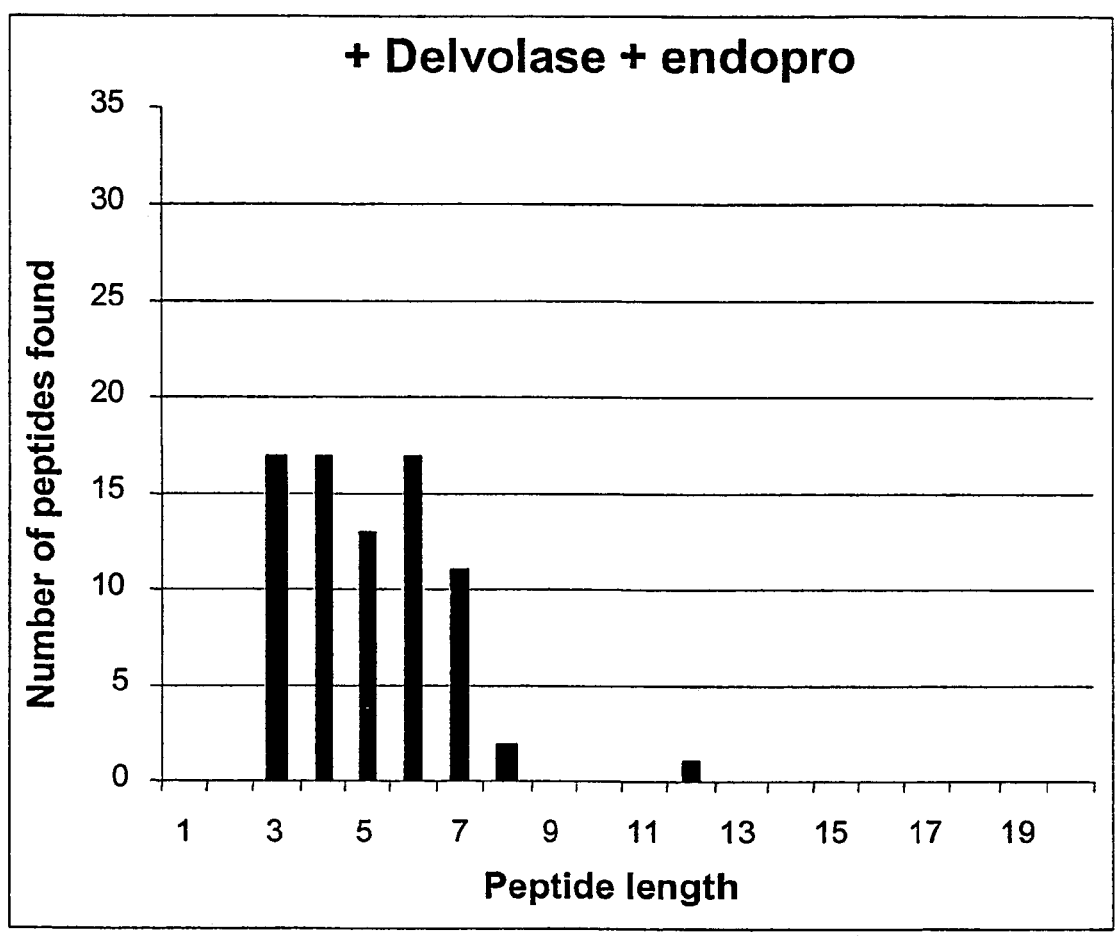
FIG. 7 shows LC/MS/MS data of a lactalbumin hydrolysate, obtained using Delvolase+proline specific endoprotease (EndoPro)
Figure 8:
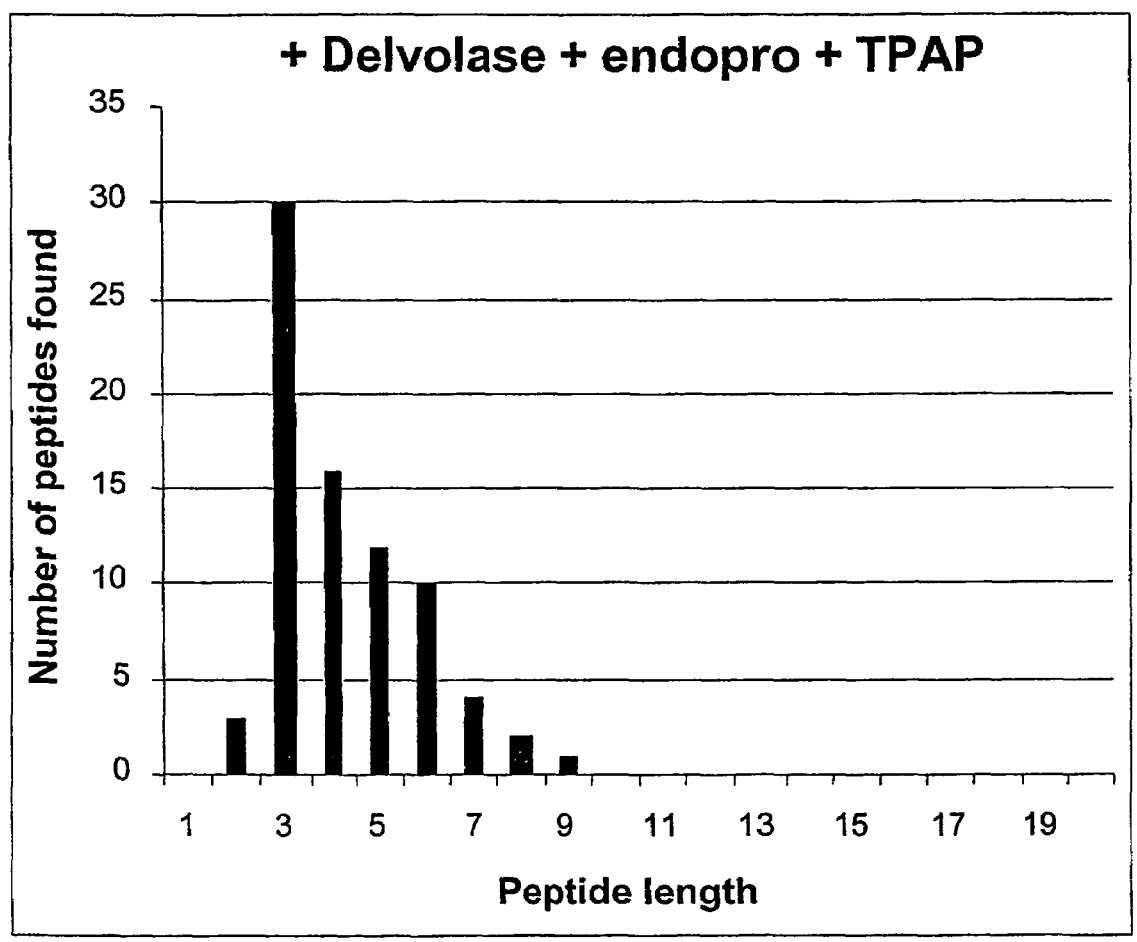
FIG. 8 shows LC/MS/MS data of a lactalbumin hydrolysate, obtained using Delvolase+TPAP-A+proline specific endoprotease (EndoPro).

In contrast with the results recorded in Example 1, the combined use of an insulin sensitizer and an amino acid-protein hydrolysate composition according to the invention results in an enhanced plasma insulin response (see FIG. 3) plus a significantly lowered blood glucose level in type 2 diabetic patients (see FIG. 4).

The invention claimed is:

1. A composition suitable for oral consumption comprising an insulin sensitizer and a peptide fraction of a protein hydrolysate, wherein at least 70 molar % of peptides in the peptide fraction have a molecular weight below 2000 Da and at least 20 molar % of peptides with a molecular weight below 2000 Da are present as di- and/or tripeptides.

2. A composition according to claim 1 further comprising at least one free amino acid selected from the group consisting of leucine, phenylalanine and arginine.

3. A composition according to claim 1, wherein the peptide fraction is comprised of peptides having molecular weights below 500 Da.

4. A composition according to claim 1, wherein most of the di- and/or tripeptides are comprised of proline at one end.

5. A composition according to claim 1, wherein at least 20% of proline present in the hydrolyzed protein is present in the di- and/or tripeptides.

6. A composition according to claim 1, wherein at least 30% of the tripeptides have a carboxy terminal proline.

7. A composition according to claim 1, wherein the insulin sensitizer is chromium, vanadium, niacin, corosilic acid, banana leaf extract, ginseng berry, Ginsensoside Re, cinnamon, methylhydroxy chalcone polymer, pterostilbene, biguanide or thiazolidinedione.

8. A dietetic product, or a pharmaceutical product, or a food or a food supplement comprising the composition according to claim 1.

9. A method of using a composition according to claim 1 which comprises having a subject ingest the composition.

10. A method of reducing insulin resistance using a composition according to claim 1 which comprises having a subject ingest the composition.

11. A method according to claim 9, wherein the composition further comprises at least one free amino acid which is selected from the group consisting of tyrosine, leucine, phenylalanine and arginine.

12. A method of treating type 2 diabetes which comprises drinking a composition according to claim 1 by a subject in need thereof.

13. A method of delaying development of diabetes which comprises drinking a composition according to claim 1 by a subject in need thereof.

14. A composition according to claim 4 further comprising at least one free amino acid selected from the group consisting of leucine, phenylalanine and arginine.

15. A composition according to claim 5 further comprising at least one free amino acid selected from the group consisting of leucine, phenylalanine and arginine.

16. A composition according to claim 6 further comprising at least one free amino acid selected from the group consisting of leucine, phenylalanine and arginine.

17. A method according to claim 10, wherein the composition further comprises at least one free amino acid which is selected from the group consisting of tyrosine, leucine, phenylalanine and arginine.

18. A method of reducing insulin resistance or delaying development of diabetes using a composition comprised of a peptide fraction of a protein hydrolysate, the method comprising:
 (a) providing the composition to a subject in need thereof and
 (b) having the subject ingest the composition whereby insulin resistance is reduced or development of diabetes is delayed.

19. A method of treating type 2 diabetes using a composition comprised of a peptide fraction of a protein hydrolysate, the method comprising:
 (a) providing the composition to a subject being treated for type 2 diabetes with an insulin sensitizer and
 (b) ingesting the composition whereby blood glucose is lowered.

20. A method according to claim 19, wherein the peptide fraction further comprises at least one free amino acid which is selected from the group consisting of tyrosine, leucine, phenylalanine and arginine.

* * * * *